United States Patent [19]
Kavoussi et al.

[11] Patent Number: 5,215,760
[45] Date of Patent: Jun. 1, 1993

[54] SATURATED SOLUTION OF PURIFIED SODIUM CHLORIDE IN PURIFIED ALOE VERA FOR INDUCING AND STIMULATING HAIR GROWTH AND FOR DECREASING HAIR LOSS

[76] Inventors: Howard Kavoussi; Harold P. Kavoussi, both of 5353 Los Robles, Laverne, Calif. 91750

[21] Appl. No.: 881,534

[22] Filed: May 12, 1992

[51] Int. Cl.$^5$ .................. A61K 33/14; A61K 7/06; A61K 35/78; A61K 31/717
[52] U.S. Cl. ........................ 424/680; 424/74; 424/195.1; 424/DIG. 4; 514/54; 514/880
[58] Field of Search .................. 424/195.1, 74, 663, 424/680, DIG. 4; 514/880, 54

[56] References Cited

U.S. PATENT DOCUMENTS 4,957,987  9/1990  McAnalley .................. 514/54

FOREIGN PATENT DOCUMENTS 1596818  7/1970  France .................. 424/680

*Primary Examiner*—John W. Rollins

[57] ABSTRACT

Composition in the form of a solution for inducing and stimulating hair-growth and for decreasing hair loss, said solution is a 100% saturation of purified sodium chloride fully dissolved in purified Aloe Vera.

2 Claims, No Drawings

SATURATED SOLUTION OF PURIFIED SODIUM CHLORIDE IN PURIFIED ALOE VERA FOR INDUCING AND STIMULATING HAIR GROWTH AND FOR DECREASING HAIR LOSS

BACKGROUND OF THE INVENTION

1. Field of the Invention

The present invention relates to a novel hair treatment composition suitable for use in accelerating the growth of hair. More specifically, it relates to a novel hair treatment composition containing, as an effective ingredient, purified Aloe Vera and Sodium Chloride.

2. Description of the Prior Art

The possession of a healthy and profuse head of hair throughout life is the ambition of most human beings. Various kinds of hair dressings, including hair treatment compositions, have been used for slowing down or stopping epilation or depilation (i.e., the involuntary loss of hair and subsequent balding). It is considered that epilation is related with abnormalities in the capillary vessels, hair follicles, and epidermis skin due to changes in, for example, the endocrine system, autonomic nervous system, and blood circulation system. To prevent or alleviate the above-mentioned abnormalities, various agents for example, skin hyperergasia agents such as female hormones, vitamins, amino acids, crude drug extracts, various bactericides, keratolysis agents, and sensitizing dyes, and peripheral nervous stimulators such as menthol have been used in hair tonic compositions. However, at present there are no truly effective agents for alleviating epilation and accelerating the growth of hair.

SUMMARY OF THE INVENTION

Accordingly, an object of the present invention is to provide a novel hair treatment composition capable of effectively accelerating the growth of hair.

In accordance with the present invention, there is provided a hair treatment composition containing, as an effective ingredient, Purified Aloe Vera and Sodium Chloride.

DETAILED DESCRIPTION OF THE PREFERRED EMBODIMENTS

The present invention relates to means for treating the scalp and more particular to compositions of matter for treatment insuring to the hair system a normal development. The composition of matter according to the invention is suited for both men's and women's hair.

The present invention has more particularly for its object a composition of matter in which the combination of ingredients provides for salt and fluid retention, by literally introducing salt and fluid to the dermis; sodium chloride from the active ingredient, fluid from the Aloe Vera gel. Since water passes freely through most biological membranes, all fluids in the body are in osmotic equilibrium. The osmolarity of plasma sample is thus roughly representative of the osmolarity of the other body fluids. The osmotic pressure of extra cellular fluid is due primarily to $Na^+$ and its accompanying anions, $Cl^-$ and $HCO^+_3$. Since $Na^+$ is the principal osmotically active cation, doubling the sodium concentration provides a good estimation of serum osmolality. Thus, the normal range of plasma $Na^+$ values is 135-145 m Eq/l (about 3.1-3.3 g/l) and the normal plasma osmolality is about 270-290 mOsmol/kg (corresponding to an osmotic pressure of 6.8-7.3 atmospheres and a freezing point depression of 0.50-0.54° C.

The application of the solution according to the present invention provides the necessary nutritive elements by the action of the active ingredient, sodium chloride, providing for a higher salt concentration in the extra-vascular space, which creates a positive osmotic gradient for fluid-serum (plasma) to move from the intra-vascular space into the extra-vascular space where it then bathes the hair follicles with a concentrated solution of nutritive elements to stimulate the biological processes of development and re-development of the hair system.

Many treatments against hair loss have already been proposed but so far it does not appear that a true revival of the hair system by simple and cheap means has really been achieved. The means according to the invention need neither complicated apparatus or processes nor specialized staff.

According to present invention, improved results are obtained by using a simple technique and more especially by the application of a composition of matter formed of a solution containing basically purified Aloe Vera and sodium chloride, which action develops at the level of keratin and roots of the hair, stopping the hair loss, stimulating the nourishment, especially during growth and regeneration. By the phrase "purified Aloe Vera", we mean the active chemical substance in the Aloe plant, CARRISYN® extract dissolved in water to a 1% (w/v) thick gel.

According to present invention, there is made on the scalp an application of a solution comprising the following ingredients: Purified Aloe Vera mixed with a 100% saturation of sodium chloride.

Various other objects, features and attendant advantages of the present invention will be more fully appreciated as the same becomes better understood from the following detailed description of the present invention.

Reference will be made to the scalp, as an illustration, but experience has proven that the means of the invention may be useful for other areas of the skin.

A solution is prepared by mixing at room temperature purified Aloe Vera and sodium chloride to a 100% saturation. One skilled in the art will appreciate the fact that different levels of saturation will provide the desired therapeutic effects. Other levels of saturation will undoubtedly occur to those skilled in the art and thus, the foregoing description does not limit the possible applications. Carrisyn (®) extract is prepared in the following manner: An Aloe Leaf is washed, sliced open and filleted. The clean inner gel is retained while the green rind and latex materials are discarded. The filleted material is homogenized and extensively filtered with a Finisher Model 75 (FMC, Chicago, Ill.), to remove most of the pulp. The clear, viscous gel is acidified to a pH of approximately 3.20 with dilute HCl to solubilize the oxalates and lactates of calcium and magnesium that are usually present to their corresponding water soluble acids. The acid treated gel is then extracted for 4-5 hours with four volumes of 95% ethanol at ambient temperature. Floating fibers are removed, then the alcohol/water mixture is siphoned off while the solid precipitate is collected by centrifugation. Most alcohol/water soluble substances such as organic acids, oligosaccharides, monosugars, anthraquinones, and inorganic salts are eliminated in the process. The solid is then washed with fresh alcohol, centrifuged, freeze dried, and ground to a white amorphous powder. Purified Aloe Vera is obtained by dissolving 1% (w/v)

CARRISYN (®) extract in water with vigorous shaking for several hours. A thick gel is obtained with a PH of (6.0). 100 parts by weight of this gel dissolve 35.8 parts of sodium chloride, converting the gel to a liquid solution, eliminating coagulation as a factor. One skilled in the art will appreciate the fact that sodium chloride is used universally as a preservative ensuring the solution's freshness; and sodium chloride in solution guards against bacterial degradation. The solution may cause slight burning and irritation; however that does not take away from its therapeutic effectiveness. Purified Aloe Vera is used because of its rapid and complete penetration into the scalp and skin. Purified sodium chloride is used because it completely dissolves in Aloe Vera and is carried with it into the scalp and skin to the hair follicles. Purified Aloe Vera has a dual role of acting as a vehicle carrier and a provider of fluid to the dermis. The sodium chloride is the active ingredient.

In addition to the above-mentioned active ingredients, various conventional ingredients suitably used in the formulation of a hair tonic composition or a hair dressing composition can be incorporated in a conventional amount into the hair tonic composition of the present invention. Typical examples of such ingredients are cantharis tincture, Jaborandi tincture, Japanese green gentian (Swertia Japonica) extract, follicle hormones, vitamin E, nicotinic acid derivatives, other vitamins such as vitamin B groups, amino acids such as serine and methionine, acetyl choline derivatives, cepharanthine, photosensitizing dyes, menthol, salicylic acid, resorcinol, beeswax, cetanol, triethanol amine, borax, lower alcohol esters of C to C saturated fatty acids, cetanol amine, glycerol monostearate, glycerol, isopropyl myristate, caster oil, citric acid, plant gums, and perfumes. These ingredients can be optionally incorporated into the hair tonic composition of the present invention unless the desired effect of the present invention is impaired.

The final forms of the hair tonic composition according to the present invention can be any conventional form of hair tonic or hair dressing compositions such as hair lotion, hair cream, hair liquid, hair oil, pomade, and hair stick. Other forms can also be utilized.

When the hair treatment composition according to the present invention is applied to the human scalp or animal skins, strong hair growth acceleration effects can be provided. That is, when the hair treatment composition according to the present invention is applied to the human scalp, depilation and epilation can be effectively alleviated and downy hairs become healthy.

The nonpathogenicity of the hair treatment composition according to the present invention has been confirmed. That is, cellulose disks 6 mm is diameter and 1 mm in thickness impregnated with 20 ul of 0.02M phosphate buffer (pH 8.0) containing 1 ml of the Purified Aloe Vera/Sodium Chloride mixture obtained according to example 1 were put on the inside upper arms of 10 humans or the shorn backs of four rabbits and fixed with tape. The cellulose disks were replaced once a day for three days. Cellulose disks impregnated with the above-mentioned buffer but containing no Purified Aloe Vera/Sodium Chloride mixture were used as a control. No abnormal conditions were found in any case.

EXAMPLES

The present invention will now be further illustrated by, but is by no means limited to, the following examples, in which the preparation, application, and effect of the hair treatment composition of the present invention are specifically disclosed.

EXAMPLE 1

Preparation of Carrisyn ® Extract

An Aloe leaf was washed, sliced open and filleted. The clean inner gel was retained while the green rind and latex materials were discarded. The filleted material was homogenized and extensively filtered with a Finisher Model 75 (FMC, Chicago, Ill.), to remove most of the pulp. The clear, viscous gel was acidified to a pH of approximately 3.20 with dilute HCl to solubilize the oxalates and lactates of calcium and magnesium that are usually present to their corresponding water soluble acids. The acid treated gel was then extracted for 4–5 hours with four volumes of 95% ethanol at ambient temperature. Floating fibers were removed, then the alcohol/water mixture was siphoned off while the solid precipitate was collected by centrifugation. Most alcohol/water soluble substances such as organic acids, oligosaccharides, monosugars, anthraquinones, and inorganic salts were eliminated in the process. The solid was then washed with fresh alcohol, centrifuged, freeze dried, and ground to a white amorphous powder.

EXAMPLE 2

The Carrisyn ® extract preparation obtained according to Example 1 was dissolved in water to a 1% (w/v) thick gel. Purified Aloe Vera was obtained by dissolving 1% (w/v) Carrisyn ® extract in water with vigorous shaking for several hours. A thick gel is obtained with a Ph of (6.0). 100 parts by weight of this gel dissolve 35.8 parts of sodium chloride, converting the gel to a liquid solution, which then is used as a hair lotion.

EXAMPLE 3

Application of Hair Tonic Composition (1) Application of hair tonic type composition to the human scalp The hair tonic type composition prepared in Example 2(1) was applied, twice a day, to the scalps of 10 men and 10 women, each suffering from large degree of itching, dandruff, and depilation at ages of 25 to 45, in an amount of 3 to 4 ml each for 6 months.

The results are as follows:

TABLE 1

| Condition | Complete Resolution | No Effect |
| --- | --- | --- |
| Dandruff | 20 | 0 |
| Depilation | 20 | 0 |
| Itching | 20 | 0 |

(2) Application of hair tonic type composition to rabbits

Three month old male rabbits were shorn on the back. The hair tonic type composition prepared in Example 2(1) was applied, twice a day, to a half-side of the shorn portion of each rabbit for one week. As a control, the base material (phosphate buffer) was also applied, twice a day, to the other half-side of the shorn portion of each rabbit for one week. The length of the grown fur was measured. The results are as follows:

TABLE 2

| Rabbit No. | Grown Fur Length | | Difference b |
|---|---|---|---|
| | Control side a | Test side a' | |
| 1 | 2.50 ± 0.08 | 2.83 ± 0.05 | 0.33 |
| 2 | 2.41 ± 0.03 | 2.63 ± 0.08 | 0.22 |
| 3 | 2.50 ± 0.09 | 2.90 ± 0.10 | 0.40 |
| 4 | 3.04 ± 0.12 | 3.38 ± 0.08 | 0.34 |
| 5 | 2.96 ± 0.04 | 3.49 ± 0.05 | 0.53 |
| 6 | 2.22 ± 0.07 | 2.85 ± 0.05 | 0.63 |
| 7 | 2.29 ± 0.09 | 2.70 ± 0.08 | 0.41 |
| 8 | 4.02 ± 0.12 | 4.55 ± 0.09 | 0.53 |
| 9 | 2.38 ± 0.07 | 2.61 ± 0.04 | 0.23 |
| 10 | 2.47 ± 0.08 | 3.04 ± 0.10 | 0.57 |
| Average | 2.68* | 3.10* | 0.42 |
| Standard Error | — | — | 0.13 |

(Remarks)
a Average fur growth length of control side (mm) standard deviation
a' Average fur growth length of test side (mm) standard deviation
b Average fur growth length of test side-average fur growth length of control side (mm)
*Mean value of average growth length of control side
*Mean value of average growth length of test side As is clear from the results shown in Table above, the hair tonic composition according to the present invention increases the fur growth rate by 15% or more as compared with the control.

We claim:

1. A hair tonic composition in the form of a solution for inducing and stimulating hair growth and for decreasing hair loss, said solution consisting essentially of a 100% saturation of crystalline sodium chloride fully dissolved in Carrisyn(®) aloe vera gel.

2. A method for inducing and stimulating hair growth or decreasing their loss in both men and women suffering from dandruff, itching and depilation comprising applying to the scalp 3 to 4 ml, twice a day, the composition as defined in claim 1.

* * * * *